United States Patent [19]
Lee et al.

[11] 4,455,530
[45] Jun. 19, 1984

[54] CONDUCTIVITY SENSOR FOR USE IN STEAM TURBINES

[75] Inventors: Pang-Kai Lee, Murrysville; William M. Hickam, Churchill; William T. Lindsay, Jr., Hempfield Township, Westmoreland County, all of Pa.

[73] Assignee: Westinghouse Electric Corp., Pittsburgh, Pa.

[21] Appl. No.: 363,757

[22] Filed: Mar. 30, 1982

[51] Int. Cl.³ ............................................. G01N 27/02
[52] U.S. Cl. ................................ 324/446; 324/65 CR; 415/118; 73/86
[58] Field of Search .................. 324/450, 446, 65 CR, 324/65 P; 357/25; 415/118; 340/406; 73/86

[56] References Cited

U.S. PATENT DOCUMENTS

| | | | |
|---|---|---|---|
| 3,058,079 | 10/1962 | Jones | 338/35 |
| 3,067,386 | 12/1962 | Freedman | 324/71 |
| 3,108,242 | 10/1963 | Scott, Jr. | 338/13 |
| 3,124,771 | 3/1964 | Rohrback | 338/13 |
| 3,148,348 | 9/1964 | Rohrback | 338/13 |
| 3,255,324 | 6/1966 | Ovshinsky | 200/61.04 |
| 3,500,059 | 3/1970 | Fielding et al. | 307/118 |
| 3,540,278 | 11/1970 | Diamond et al. | 73/336.5 |
| 3,578,409 | 5/1971 | Silverman et al. | 23/254 |
| 3,699,436 | 10/1972 | Shigematsu et al. | 324/65 R |
| 3,731,187 | 5/1973 | Hausler et al. | 324/65 R |
| 4,101,828 | 7/1978 | Dehler | 324/65 R |
| 4,140,990 | 2/1979 | Pompei Katz de Warrens | 324/446 |
| 4,266,187 | 5/1981 | Slough | 324/65 CR |
| 4,357,576 | 11/1982 | Hickam et al. | 324/450 |
| 4,386,498 | 6/1983 | Lee | 415/118 |

Primary Examiner—Michael J. Tokar
Assistant Examiner—Kevin D. O'Shea
Attorney, Agent, or Firm—D. Schron

[57] ABSTRACT

A conductivity sensor for placement on a curved steam turbine component within the steam path. The sensor includes a metal foil base over which is deposited an electrically insulating layer such as glass. The base and insulating layers are of such thickness so as to be flexible so as to conform to the curved surface. An electrode array is deposited upon the insulating layer and spaced so as to accommodate for deposition of steam impurities onto the insulating layer. Flexible links connect the electrodes to electrical leads so that conductivity indications may be obtained.

14 Claims, 7 Drawing Figures

CONDUCTIVITY SENSOR FOR USE IN STEAM TURBINES

BACKGROUND OF THE INVENTION

1. Field of the Invention

Invention in general relates to conductivity sensors or cells and particularly to one utilized in the steam path of steam turbines.

2. Description of the Prior Art

It is well known that the impurities in steam used to drive steam turbines in power plants are a corrosion concern. For example, deposition of corrosive salt impurities on steam turbine blades made lead to stress corrosion cracking failure.

Of particular concern is sodium chloride which although dissolved in the superheated steam at low concentrations can, as the steam expands through the turbine, deposit at high concentrations. Near the exit of the low pressure section of the turbine arrangement the steam undergoes an expansion whereby a consequent transition to a wet condition results. The entrained sodium chloride could then form a saturated solution which if deposited upon the turbine rotor blades could lead to corrosion and cracking.

If the location of the salt deposition zone is known, the expansion path of the steam can be shifted in such a way that the induced corrosion damage from the salt solution deposition to a specific component, or components, can be reduced or minimized. An arrangement for shifting this zone is described and claimed in U.S. Pat. No. 4,386,498 and various conductivity sensors for determining the salt deposition zone are described and claimed in U.S. Pat. No. 4,357,576, both applications having the filing date of Oct. 15, 1980 and both being assigned to the same assignee of the present invention.

In various monitoring situations it would be desirable to mount the conductivity sensor directly onto a turbine blade and although various types of sensors and probes are illustrated in the latter application none can conform to a curvilinear surface such as encountered on a rotating or stationary turbine blade. The sensor of the present invenion is about the size of a common postage stamp and can be mounted directly on a curvilinear surface such as a turbine blade in the steam path of a steam turbine.

SUMMARY OF THE INVENTION

The sensor includes a base mountable on a curvilinear section of the turbine directly in the steam path. The base is comprised of a relatively flexible metal foil so as to conform to the curvilinear surface. An electrically insulating layer is disposed over an exposed surface of the base and is of a thickness so as to be relatively flexible after its application to the base. An electrode array is deposited on the insulating layer and is of a particular thickness to allow flexing with the insulating layers and base. The electrodes are of a sufficient thickness and are spaced from one another at a particular distance to allow deposition of steam impurities on the insulating layer and between the electrodes to establish an electrically conducting path therebetween.

DESCRIPTION OF THE PREFERRED EMBODIMENTS

Figure 1:
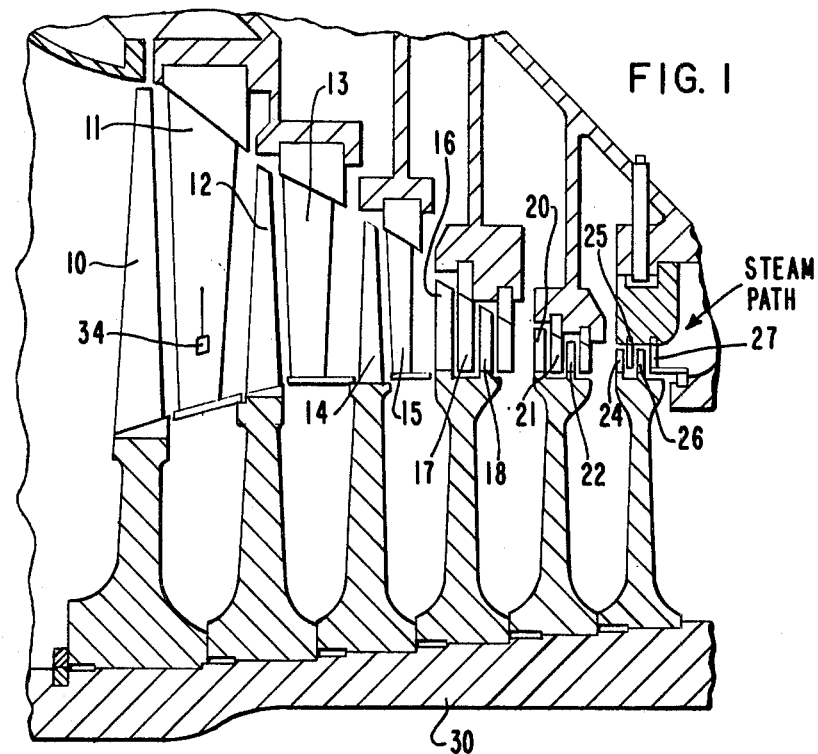
FIG. 1 is a cross-sectional view through a portion of a typical low pressure steam turbine.

A common type of steam turbine system includes a plurality of turbines in the form of a high pressure turbine, an intermediate pressure turbine and a low pressure turbine and although the sensor of the present invention may be placed within any one of these turbines for detecting various impurities such as sodium hydroxide it will be described by way of example with respect to the detection of a salt solution zone which is encountered in the low pressure turbine, a portion of which is illustrated in FIG. 1.

The turbine includes a plurality of turbine blades 10 to 27 with the even numbered blades being connected to rotor 30 and constituting rotor blades, while the odd numbered blades are connected to an inner turbine cylinder and constitute stationary blades.

In a typical operation, superheated dry steam enters the first stage (constituted by blades 26 and 27) and passes through subsequent stages where expansion and temperature and pressure changes take place. At approximately the last stage (constituted by blades 10 and 11) or next to the last stage (blades 12 and 13) depending upon operating conditions, there is a transition zone where the dry steam converts to a moist fog-like condition and any entrained sodium chloride precipitates out into a relatively narrow salt solution zone which can cause stress corrosion and cracking problems. The salt solution zone shifts under different operating conditions and upstream of the zone dry solid sodium chloride is stable in the presence of superheated steam and does not have the corrosive effects, whereas downstream of the zone in the wet region, the salt contamination is so dilute that it has no corrosive effects.

Figure 2:
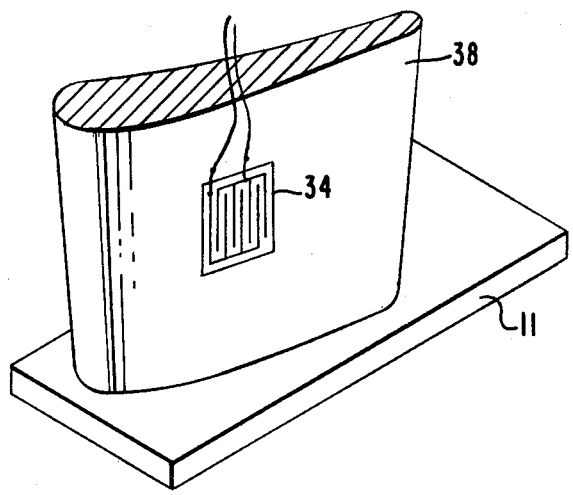
FIG. 2 is a more detailed view of one of the turbine blades of FIG. 1.
Figure 3:
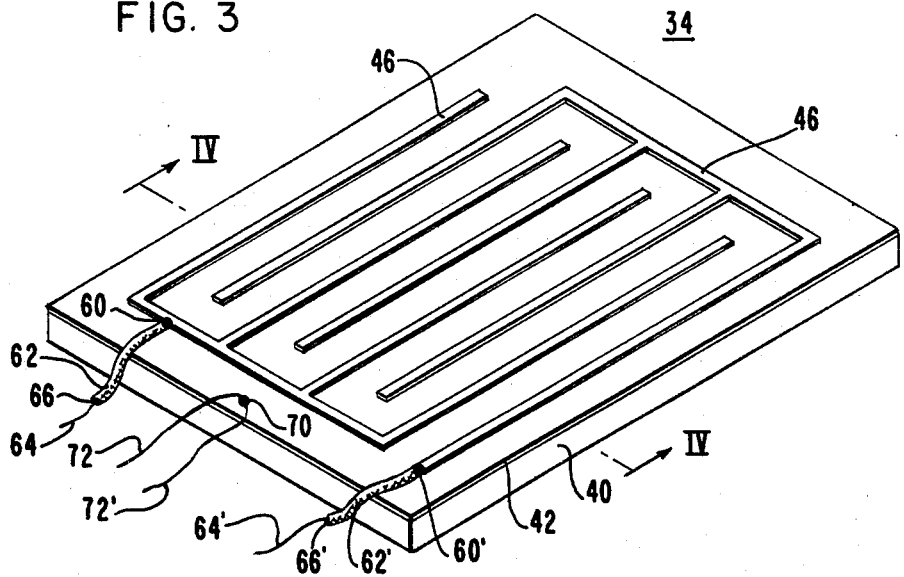
FIG. 3 is a view of one embodiment of the present invention.

It would be desirable to know the position of this salt solution zone relative to the blades and accordingly a conductivity sensor 34 in accordance with one aspect of the invention is affixed to one of the turbine blades, illustrated as stationary blade 11. As illustrated in FIG. 2, blade 11 has a curvilinear surface 38 to which the sensor 34 is affixed. Such placement of a sensor is suggested in U.S. Pat. No. 4,386,498 however no structure is described that will withstand the hostile environment within the turbine and which will conform to the curvature of the turbine blade. One sensor which will meet these objectives is illustrated in FIG. 3 as well as the cross-sectional view of FIG. 4.

The sensor includes a base 40 of a material capable of withstanding temperatures which may reach hundreds of degrees centigrade in many turbine systems. The base however, must be sufficiently flexible so as to conform to the curvature of the surface on which it is mounted. In a preferred embodiment the base is a metal foil having a thickness range of approximately 2 or $3\times10^{-3}$ inches to $5\times10^{-3}$ and an area of approximately $\frac{1}{2}$ to $\frac{3}{4}$ square inches. Typical metal foils which may be utilized include stainless steel, high chromium alloys, as well as titanium alloys. Above the higher thickness value the foil may be too rigid to conform to the various curvilinear surfaces whereas below the lower limit value the device may be too limp to properly handle.

Disposed over the base 40 is an electrically insulating layer 42 of a material which will adequately bond to the metal foil base and which is of a particular thickness so as to provide for adequate electrical insulation and yet be fexible so as to bend with the base. In one embodiment insulating layer 42 may be a glass layer such as Corning Glass 7059 applied by a sputtering technique which involves ejection of atoms or molecules from a target followed by deposition of the ejected atoms or molecules onto the metal foil substrate. The glass may be sputtered to an approximate thickness of from $0.2 \times 10^{-3}$ inches to $0.3 \times 10^{-3}$ inches. As an alternative, the insulating layer may be alumina which may be applied by the sputtering technique or which may be flame sprayed wherein alumina powder is fed into an oxygen-gas flame cone and propelled by the expulsion of the burning gases from a rocket nozzle. The thickness of the alumina insulating layer will generally be greater than that of glass and may obtain a maximum of approximately $1 \times 10^{-3}$ inches.

During the insulating layer coating process the reverse side of the metal foil base may become oxidized. Since the sensor will be affixed to a turbine part of means of a high temperature adhesive, it is desirable that the oxide film be removed so as to ensure for better adhesion. The removal of the oxide film may be accomplished with the aid of a fine grade emery paper followed with a degreasing step.

A metallic electrode array 46, 46' is deposited over the insulating layer 42 and in one embodiment, as illustrated in FIG. 3 the electrode array takes the form of interdigitated fingers. The electrodes are of a material which is non-corrodible in the steam atmosphere and they are of a thickness to allow flexible bending. In one embodiment the inter-digitated electrode array may be thin film gold electrodes in the range from approximately $10 \times 10^{-6}$ inches to $20 \times 10^{-6}$ inches and applied by a sputtering technique with a subsequent photo etching of the desired electrode pattern.

In order to enhance the bonding between the gold electrodes and the insulating layer a prime coating 48 of chromium may be applied to the insulating layer 42 and may be in the thickness range of approximately $1 \times 10^{-6}$ to $2 \times 10^{-6}$ inches with the deposition of the chromium being accomplished by a sputtering technique.

Figure 4:
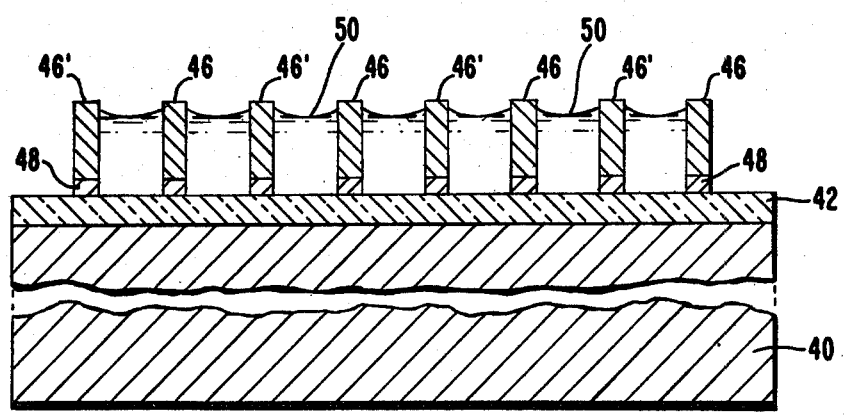
FIG. 4 is a cross-sectional view along the line IV—IV of FIG. 4.

As best illustrated in FIG. 4, the electrodes 46, 46' are spaced at a sufficient distance from one another to allow for deposition of steam impurities such as a sodium chloride solution 50. Not only may the presence of the sodium chloride solution be detected by the change in conductance between electrodes but the rate of deposition of such solution may also be determined.

The electrical connections to the sensor are illustrated in FIG. 3 and include terminals 60 and 60' which may be fabricated as part of the electrode array. Short links of gold ribbon 62 and 62' are bonded to respective terminals 60 and 60' such as by ultrasonic welding and form a flexible link between the electrode array and electrical leads 64, 64', with the connection between the links and leads being affected by means of conductive adhesive silver epoxy or silver glass 66 and 66'.

Figure 5:
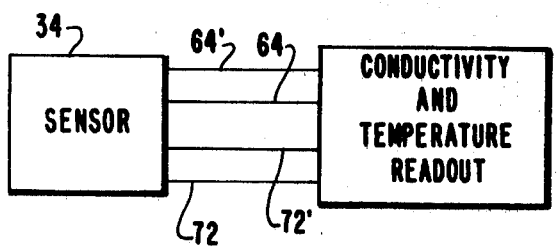
FIG. 5 is a block diagram illustrating the sensor in conjunction with a read out.

In order to make a relatively adequate conductivity determination, it is preferable that the temperature at the sensor be known. Accordingly, a thermocouple 70 is provided and is affixed to the sensor such as by a high temperature adhesive. Thermocouple leads 72, 72' as well as the sensor leads 64, 64' are provided to a measuring unit containing a temperature readout and conductivity bridge circuit such as illustrated in FIG. 5, so that a determination of temperature and conductivity may be obtained. From this determination parameters of the turbine system may be varied so as to move or vary the salt solution zone, as described in the aforementioned U.S. Pat. No. 4,386,498.

Figure 6:
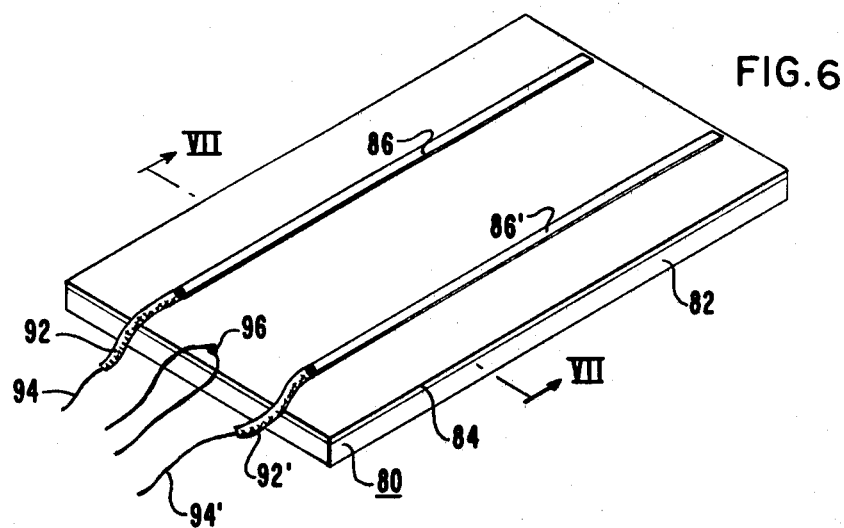
FIG. 6 is a view of another embodiment of the present invention.
Figure 7:
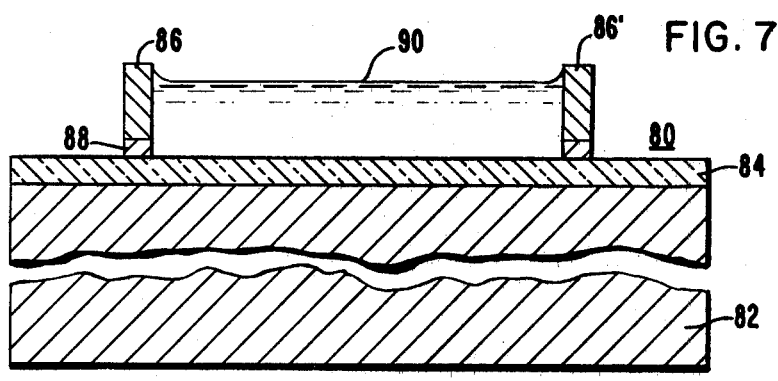
FIG. 7 is a cross-sectional view taken along the lines VII—VII of FIG. 6.

FIG. 6 and the cross-sectional view of FIG. 7 illustrate an alternate electrode arrangement which may be utilized. The conductivity sensor 80 includes a base 82 which may be identical so that described with respect to FIGS. 3 and 4. The electrically insulating layer 84 may for this embodiment be alumina deposited to a thickness of approximately $1 \times 10^{-3}$ inches. Two electrodes 86 and 86' are illustrated and are solid metal strips affixed to the electrically insulating layer by means of a high temperature adhesive 88 such as Epoxylit 810 of the Epoxylit Corporation, Anaheim, Calif. The metal strip electrodes are preferably of platinum although solid stainless steel and other alloys may be utilized. The thickness of the platinum electrodes may range from approximately 3 times $10^{-3}$ inches to $5 \times 10^{-3}$ inches with the spacing therebetween of approximately $10 \times 10^{-3}$ inches to $30 \times 10^{-3}$ inches to allow for deposition of the electrolytic salt solution 90 (FIG. 7).

As best seen in FIG. 6, a flexible link in the to form of platinum wires 92, 92' may be affixed to the platinum electrodes such as by welding and the links thereafter electrically connected to leads 94, 94' such as by welding or soldering. As was the case with respect to the sensor of FIG. 3, the sensor of FIG. 6 also includes a thermocouple 96 affixed to the same surface to which the electrodes are affixed.

Accordingly, there has been described a conductivity sensor which is rugged enough to endure the harsh environment within the steam path of a turbine system and which will provide an indication of electrolyte deposition. The sensor can conform to various curved surfaces such as turbine blades and is of a size so as to be relatively non-obtrusive. When applied to a stationary turbine blade the sensor's electrical leads may be positioned along the blade length to be connected with external conductivity measuring equipment. If utilized on a rotating turbine blade conventional telemetry techniques would apply.

We claim:

1. A conductivity sensor for in situ measuring of impurities in steam used to drive steam turbines comprising:

(A) a base mountable on a portion of said turbine directly in the steam path;

(B) said base being comprised of a relatively flexible metal foil so as to conform to a curvilinear surface of a turbine part in the steam path;

(C) an electrically insulating layer disposed over a surface of said metal foil base and having a thickness so as to be relatively flexible after application to said base;

(D) a metallic electrode array on said insulating layer and having a thickness so as to allow flexing with said insulating layer and base;

(F) said electrode array being exposed to and being non-corrodible in said steam;

(G) said electrode array being of sufficient thickness and electrodes of said array being spaced from one another at a distance to allow deposition of steam impurities between said electrodes to establish an electrically conducting path therebetween.

2. Apparatus according to claim 1 wherein:

(A) said metal foil base has a thickness in the range of approximately $3 \times 10^{-3}$ inches to $5 \times 10^{-3}$ inches.

3. Apparatus according to claim 2 wherein:

(A) said metal foil base has a surface area of from approximately ½ to ¾ square inches.

4. Apparatus according to claim 2 wherein:

(A) said insulating layer has a thickness in the range of approximately $0.2 \times 10^{-3}$ inches to $0.3 \times 10^{-3}$ inches.

5. Apparatus according to claim 4 wherein:

(A) said insulating layer is glass.

6. Apparatus according to claim 4 wherein:

(A) said insulating layer ia alumina.

7. Apparatus according to claim 2 wherein:

(A) said electrode array is a thin film array having a thickness in the range of approximately $10 \times 10^{-6}$ inches to $20 \times 10^{-6}$ inches.

8. Apparatus according to claim 2 wherein:

(A) said electrode array is comprised of discrete metal electrodes adhesively affixed to said insulating layer.

9. Apparatus according to claim 7 includes:

(A) A primer layer disposed on said insulating layer; and wherein (B) said electrode array is deposited on said primer layer.

10. Apparatus according to claim 1 wherein:

(A) said base is affixed to a curved turbine blade.

11. Apparatus according to claim 1 which includes:

(A) a first flexible electrically conducting link connected to one electrode of said array; and (B) a second flexible electrically conducting link connected to another electrode of said array.

12. Apparatus according to claim 11 which includes:

(A) conductivity measuring circuitry; and (B) electrically conducting leads connecting said measuring circuitry with said first and second flexible links.

13. Apparatus according to claim 1 which includes:

(A) a temperature sensor element mounted on said conductivity sensor.

14. Apparatus according to claim 13 wherein:

(A) said temperature sensor element is adhesively affixed to said insulating layer.

* * * * *